United States Patent
Van Der Zaag et al.

(10) Patent No.: US 8,399,855 B2
(45) Date of Patent: Mar. 19, 2013

(54) PHOTODIODE FOR DETECTION WITHIN MOLECULAR DIAGNOSTICS

(75) Inventors: Pieter Jan Van Der Zaag, Eindhoven (NL); Ian French, Brighton (GB); Nigel David Young, Redhill (GB)

(73) Assignee: Koninklijke Philips Electronics N.V., Eindhoven (NL)

( * ) Notice: Subject to any disclaimer, the term of this patent is extended or adjusted under 35 U.S.C. 154(b) by 415 days.

(21) Appl. No.: 12/374,000

(22) PCT Filed: Jul. 5, 2007

(86) PCT No.: PCT/IB2007/052630
§ 371 (c)(1),
(2), (4) Date: Jan. 15, 2009

(87) PCT Pub. No.: WO2008/012705
PCT Pub. Date: Jan. 31, 2008

(65) Prior Publication Data
US 2009/0250630 A1 Oct. 8, 2009

(30) Foreign Application Priority Data
Jul. 21, 2006 (EP) .................... 06117619

(51) Int. Cl.
*G01N 21/64* (2006.01)
(52) U.S. Cl. .................................. 250/458.1
(58) Field of Classification Search ........... 250/458.1
See application file for complete search history.

(56) References Cited

U.S. PATENT DOCUMENTS

| 4,496,788 A * | 1/1985 | Hamakawa et al. ......... 136/249 |
| 6,379,622 B1 | 4/2002 | Polak et al. |
| 6,867,420 B2 | 3/2005 | Mathies et al. |
| 6,995,386 B2 | 2/2006 | Emoto |
| 2003/0116814 A1 | 6/2003 | Kuhara et al. |
| 2003/0222223 A1 | 12/2003 | Kamei et al. |
| 2005/0042665 A1 | 2/2005 | Gilmanshin |
| 2005/0157301 A1 | 7/2005 | Chediak et al. |
| 2005/0237524 A1 * | 10/2005 | Kamei et al. .................. 356/318 |
| 2006/0169878 A1 * | 8/2006 | Kasano et al. ................ 250/226 |

FOREIGN PATENT DOCUMENTS

JP 60130870 A 7/1985

* cited by examiner

Primary Examiner — Constantine Hannaher

(57) ABSTRACT

A photodiode (200), for instance a PN or a PIN photodiode, is disclosed. The photodiode receives incident radiation having first and second spectral distributions, where the first spectral distribution is spectrally shifted from the second spectral distribution. The photodiode has a first semiconductor layer (211) capable of absorbing incident radiation (231) having a first spectral distribution without generating a photocurrent, while simultaneously transmitting incident radiation having a second spectral distribution to the intrinsic layer (212) for generating a photocurrent (213). The photodiode may be used in connection with detecting the presence of target molecules that has been labeled with labeling agents, such as fluorophores or quantum dots. The labeling agents are characterized by the Stokes shift and, therefore, they emit fluorescent radiation having the second spectral distribution that is spectrally shifted from the illumination radiation having the first spectral distribution.

17 Claims, 6 Drawing Sheets

PHOTODIODE FOR DETECTION WITHIN MOLECULAR DIAGNOSTICS

FIELD OF THE INVENTION

The invention relates to a photodiode, and in particular to a photodiode for detection within molecular diagnostics.

BACKGROUND OF THE INVENTION

Biological samples can be analyzed by illuminating the biological sample with a beam of light and detecting the scattered light. In order to be able to detect a presence or absence of a particular biological specimen or molecule, for instance DNA, RNA, cells and antibodies, of the biological sample the fluorescence method is useful. The fluorescence method utilizes labeling agents that are capable of binding to particular sites of a molecule of the biological sample. When the sample is illuminated with a beam of light the labeling agent will emit light at a wavelength different from the wavelength of the illumination beam.

By utilizing the capability of specific target molecules from the sample to be analyzed to bond to corresponding probe molecules, that for instance are present in a detection system, the presence or absence of the specific target molecule can be determined. For instance, if the target molecules are labeled with a labeling agent, and if the target molecules subsequently bind to a probe molecule, the presence of the target molecule can be verified if fluorescent light is detected. Examples of such target-probe molecule pairs are antibody-antigen, cell-antibody combinations and receptor-ligands pairs. Further examples include bonding or hybridization of for instance DNA-DNA pairs, RNA-RNA pairs and DNA-RNA hybrids.

In order to detect the emitted light from the labeling agent, the detection system must be capable of detecting radiation having a particular wavelength of emitted radiation originating from the labeled agents. This is a problem since the biological sample typical will emit light both having the wavelength of the illumination light and the emitted light from the labeling agents. Accordingly, a method capable of discriminating between the wavelengths of the illumination light and the emitted light from the labeling agents would be advantageous.

At the same time it would be beneficial to have a simple method for discriminating between the wavelengths of the illumination light and the emitted light.

U.S. Pat. No. 6,867,420 discloses a miniaturized optical excitation and detector system for detecting fluorescently labeled analytes in electrophoretic microchips and microarrays. The system uses miniature integrated components, light collection, optical fluorescence filtering, and an amorphous a-Si:H detector for detection. The collection of light is accomplished with proximity gathering and/or a micro-lens system. Optical filtering is accomplished by integrated optical filters. U.S. Pat. No. 6,867,420 discloses a detection system where the emitted light it filtered by an integrated optical filter and detected with a photo detector. However, the detection system in U.S. Pat. No. 6,867,420 is not simple.

Hence, an improved detection system would be advantageous, and in particular a more efficient and/or reliable detection system would be advantageous.

SUMMARY OF THE INVENTION

Accordingly, the invention preferably seeks to mitigate, alleviate or eliminate one or more of the above mentioned disadvantages singly or in any combination. In particular, it may be seen as an object of the present invention to provide a detection system that solves the above mentioned problems of the prior art by providing a simple detection system capable of discriminating between wavelengths.

This object and several other objects are obtained in a first aspect of the invention by providing a photodiode comprising, a first semiconductor layer doped with a first impurity, said first semiconductor layer being adapted to receive incident radiation, said incident radiation having a spectral distribution with a center wavelength of at least 350 nm, a second semiconductor layer doped with a second impurity, a third semiconductor region, said third semiconductor region being capable of generating free electrons and free holes when excited with at least part of the incident radiation, wherein the incident radiation comprises radiation having a first spectral distribution and a second spectral distribution, where the first spectral distribution is spectrally shifted from the second spectral distribution, the first semiconductor layer is capable of absorbing incident radiation having the first spectral distribution, wherein the absorption of radiation having the first spectral distribution does not significantly contribute with a photocurrent, the first semiconductor layer is capable of transmitting the incident radiation having the second spectral distribution, and the free electrons and free holes in the third semiconductor region generated by radiation having the second spectral distribution generate a photocurrent.

The invention is particularly, but not exclusively, advantageous for obtaining a simple detection system capable of discriminating between wavelengths by providing a photodiode having a first semiconductor layer capable of both absorbing incident radiation having a first spectral distribution without significantly generating a photocurrent and transmitting the incident radiation having a second spectral distribution. Accordingly, the photodiode may perform the desirable discrimination or filtering of wavelengths since the photodiode may be capable of discriminating between first and second spectral distributions by use of a simple photodiode. Accordingly, the photodiode may be capable of optically filtering away radiation having a first spectral distribution while simultaneously detecting radiation having a second spectral distribution.

It may be an advantage that the first semiconductor layer is capable of absorbing incident radiation having a first spectral distribution, wherein the absorption of radiation having the first spectral distribution does not significantly contribute with a photocurrent. Accordingly, the ratio of photocurrent of the first spectral distribution and photocurrent of the second spectral distribution is insignificant, since the ratio is smaller than 1/80, preferably smaller than 1/90 or more preferred smaller than 1/99 in accordance with the absorption percentages of the first semiconductor layer.

The photodiode may provide a simple detection system or device which, in addition, may be easily produced and, thereby, an inexpensive detection system may also be achieved by the photodiode.

It would be desirable to have a photodiode or a photo detector that is simple enough and has sufficient filtering capabilities to filter away radiation having a first spectral distribution, so that the photodiode or photo detector can be built into or integrated with a detection apparatus, such as a micro total analysis system, a lab-on-a-chip or a molecular diagnostic system (MDx). That desirable object may be solved by the photodiode according to a first aspect of the invention.

It would also be desirable to have a photodiode or a photo detector that is simple enough and sufficiently inexpensive to be utilized in a hand-held detection apparatus, such as molecular diagnostic system (MDx). That desirable object may be solved by the photodiode according to a first aspect of the invention.

It may be an advantage that the photodiode may be integrated with a detection apparatus, since this may eliminate the risk of contaminating sensitive detection electronics. It may be desirable to have a cost effective photodiode having filtering capabilities without utilizing expensive external optical filters. That objective may be achievable by the photodiode according to a first aspect of the invention.

The first semiconductor layer of the photodiode may have a thickness that is adapted to absorb the radiation having the first spectral distribution within a volume of the first semiconductor layer. Since it would be desirable to have a simple photodiode having filtering capabilities, this object may be achieved by adapting the thickness of the first semiconductor layer to absorb the radiation having the first spectral distribution, so as to obtain a filtering capability solely due to the thickness of the first semiconductor layer.

Such thickness of the first semiconductor layer may be greater than 100 nm, preferably greater than 200 nm or more preferred greater than 300 nm in order to make the photodiode capable of discriminating between first and second spectral distributions.

In other words the thickness of the first semiconductor layer may be chosen so that the first semiconductor layer may be capable of absorbing at least 80%, preferably at least 90% or more preferred at least 99% of the incident radiation having the first spectral distribution. It may be an advantage having a photodiode with a first semiconductor layer that is capable of absorbing for instance at least 99% of the incident radiation, since an absorption of at least 99% corresponds to filtering away at least 99% of the first spectral distribution.

In an embodiment the third semiconductor region may be a third layer of intrinsic semiconductor material positioned between the first semiconductor layer and the second semiconductor layer. Such a photodiode is referred to as a PIN diode or NIP diode. It may be an advantage that the photodiode is a PIN or NIP photodiode, since such photodiodes may have improved performance due a capability of generating higher photocurrent, having lower dark leakage, and higher sensitivity to incident radiation having the second spectral distribution.

The photodiode according to a first aspect of the invention may have a first semiconductor layer which is a p doped layer, doped with acceptor impurities and, accordingly, a second semiconductor which is an n doped layer, doped with donor impurities. Alternatively, the photodiode may have a first semiconductor layer which an n doped layer doped with donor impurities and, accordingly, a second semiconductor layer which is a p doped layer doped with acceptor impurities. The choice of the order of the p doped layer and the n doped layers in relation to the respective first and second semiconductor layer is applicable both to the first type of photodiodes wherein the third semiconductor region is comprised by a part of the first semiconductor layer and a part of the second semiconductor layer, and to the second type of photodiodes where the third semiconductor region is a third layer of intrinsic semiconductor material positioned between the first semiconductor layer and the second semiconductor layer.

The spectral shift between the first spectral distribution and the second spectral distribution may be at least 50 nm, preferably at least 100 nm, or more preferred at least 200 nm. It may be an advantage that the spectral shift or Stokes shift is at least 200 nm, since a large spectral shift improves the discrimination, or filtering effect, of wavelengths made by the photodiode.

The first semiconductor layer and/or the second semiconductor layer may be made of such semiconductor materials as amorphous silicon (a-Si), amorphous silicon carbide (a-SiC), microcrystalline Si and low temperature polySi. It may be an advantage that different semiconductor materials can be used for semiconductor layers, as different semiconductor materials may have different absorbing capabilities. Accordingly, by choosing a particular semiconductor material the capability of the photodiode to filter away radiation having a first spectral distribution while detecting radiation having a second spectral distribution may be optimized. Different semiconductor materials may also have other advantages, for instance, in relation to detection sensitivity, noise, costs, production attributes, etc.

The photodiode may have an antireflection coating applied on the top face of the first semiconductor layer. It may be an advantage to have an antireflection coating on the top face of the first semiconductor layer, since the antireflection coating may increase the amount of incident radiation being transmitted into the first semiconductor layer.

In a second aspect, the present invention relates to a detecting apparatus capable of detecting the presence or absence, and optionally quantity, of a target molecule of a sample of a biological substance, said detecting apparatus comprises, a processing device adapted to be provided with the sample containing target molecules, said processing device further being adapted to be provided with probe molecules for bonding with the target molecules, wherein the target molecules and/or probe molecules are labeled with labeling agents having luminescent properties, wherein said labeling agents emits radiation having a second spectral distribution when illuminated with radiation having a spectral distribution corresponding to the first spectral distribution, an illuminator capable of illuminating the sample with radiation having a spectral distribution corresponding to the first spectral distribution, and a photodiode according to a first aspect of the invention being capable of receiving emitted radiation comprising the first spectral distribution and the second spectral distribution, said emitted radiation being emitted from the sample, wherein the first spectral distribution is spectrally shifted from the second spectral distribution, the photodiode is capable of absorbing radiation having the first spectral distribution without significantly contributing with a photocurrent, said radiation being absorbed in the first semiconductor layer, and said absorption being at least 80% of the radiation having the first spectral distribution, and the photodiode is capable of generating a detectable photocurrent corresponding to the radiation having the second spectral distribution, said detectable photocurrent being caused by the generation of free electrons and free holes in the third semiconductor region when excited with the radiation having the second spectral distribution.

It would be desirable to have a detection apparatus capable of detecting the presence or absence, and optionally quantity, of a target molecule by detection of for instance fluorescent radiation from labeled target. Such a desirable object may be achieved by a detection apparatus comprising a photodiode according to a first aspect of the invention, since the photodiode may be capable of discriminating between radiation having a first spectral distribution and radiation having a second spectral distribution.

The sample of the biological substance may include such substances as cells, tissue sections, DNA, proteins, blood and urine. However, the sample may include other biological substances as well. Accordingly, the target molecule may be a molecule of the sample of the biological substance.

The direction of the radiation from the illuminator may perpendicular to the normal of the surface of the first semiconductor layer, which may be an advantage since this reduces the amount of radiation having the first spectral distribution which is incident to the photodiode.

The detection apparatus may comprise a second processing device capable of amplifying a concentration of DNA by Polymerase Chain Reaction. It may be an advantage to integrate other processing capabilities to the detection apparatus, such as Polymerase Chain Reaction, as this may increase the usability of the detection apparatus.

In a third aspect, the present invention relates to a method for detecting a target in a sample of a biological substance, said method comprises providing a detection apparatus with probe molecules for bonding with target molecules, wherein the target molecules and/or probe molecules are labeled with labeling agents having luminescent properties, wherein said labeling agents emits radiation having a second spectral distribution when illuminated with radiation having a spectral distribution corresponding to the first spectral distribution, providing the sample containing target molecules to the detection apparatus, illuminating the sample with radiation having a spectral distribution corresponding to the first spectral distribution, receiving emitted radiation from the sample by using a photodiode according to a first aspect of the invention, said emitted radiation comprising the first spectral distribution and the second spectral distribution, wherein the first spectral distribution is spectrally shifted from the second spectral distribution, the photodiode absorbs radiation having the first spectral distribution without significantly contributing with a photocurrent, said radiation being absorbed in the first semiconductor layer, and said absorption being at least 80% of the radiation having the first spectral distribution, and the photodiode generates a detectable photocurrent corresponding to the radiation having the second spectral distribution, said detectable photocurrent being caused by the generation of free electrons and free holes in the third semiconductor region when excited with the radiation having the second spectral distribution.

The first, second and third aspect of the present invention may each be combined with any of the other aspects. These and other aspects of the invention will be apparent from and elucidated with reference to the embodiments described hereinafter.

BRIEF DESCRIPTION OF THE FIGURES

The present invention will now be explained, by way of example only, with reference to the accompanying Figures, where.

DETAILED DESCRIPTION OF AN EMBODIMENT

Figure 1:
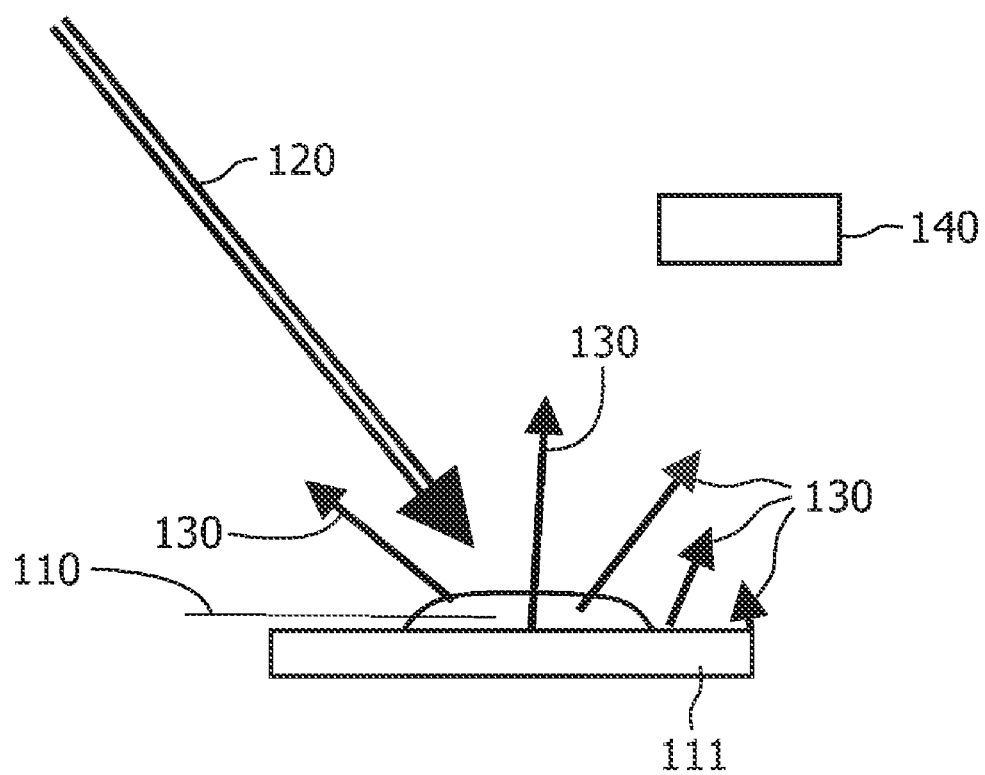
FIG. 1 is an illustration of a fluorescent detection system.

FIG. 1 is an illustration of a fluorescent detection system where a sample or analyte 110 of biological material, placed on some plate 111 or in a container 111, is illuminated with an illumination beam 120. Emitted radiation in the form of scattered, reflected, diffracted, luminescent and/or fluorescent radiation 130 from the sample 110 and the plate 111 is detected by the detector 140.

The sample 110 contains target molecules that have reacted with probe molecules so that the targets bonds to the probes. The probe molecules may have been provided on the plate 111, so that the probes stick to the plate 111, prior to applying the sample 110 to the plate 111. Examples of target molecule and probe molecule pairs are antibody-antigen pairs, cell-antibody combinations, strands of DNA pairs, strands of RNA pairs, antibody-antigen pairs and receptor-ligands pairs.

The target molecules, or the probe molecules, can be provided or conjugated with labeling agents having luminescent or fluorescent properties. Accordingly, if the target molecules match the probe molecules, the target molecules will bond to the probe molecules. By washing away any non-reacted target molecules, so that only reacted target-probe pairs remains (assuming that the sample contained targets capable of bonding to the stuck probes), the presence, the absence, and optionally the quantity, of target molecules can be verified by detecting the luminescent or fluorescent emitted radiation from the labeling agents.

Alternatively, the probes can be provided or conjugated with labeling agents having luminescent or fluorescent properties. The labeling agents attached to the probes have the property to emit fluorescent radiation only when the corresponding probes have reacted with matching targets.

When the sample 110 has been labeled with fluorescent labeling agents, the emitted radiation 130 contains radiation in the form of fluorescent radiation originating from the labeled agents. However, the emitted radiation 130 also contains radiation in the form in of scattered, reflected and/or diffracted radiation. Part of the illumination beam 120 is absorbed by the labeling agents and re-emitted as radiation having a wavelength different from the wavelength of the illumination beam 120 due to fluorescence. Other part of the illumination beam 120 causes scattering, reflection, diffraction for instance from the plate or container 111 or from other parts of the biological sample 110. Accordingly, the emitted radiation 130 will contain radiation having a first spectral distribution Wi primarily due to scattering, reflection and diffraction, and the emitted light 130 will also contain light having a second spectral distribution Wf due to fluorescence. Here and in the following, when reference is made to a sample that has been labeled, this should equally be understood as the targets of sample have been labeled.

The first spectral distribution Wi may be equal to, or correspond to, the spectral distribution Wib of the illumination beam 120. Due to absorption of light in the sample 110 and the plate 111 or container 111 the first spectral distribution Wi may differ from the spectral distribution Wib of the illumination beam 120. However, the spectral distribution Wib of the illumination beam 120 can be said to correspond to the first spectral distribution Wi or vice versa.

The labeling agents have the capability of absorbing incident radiation from the illumination beam 120 having the spectral distribution Wib, and subsequently, in response to absorbing light, emitting light having the second spectral distribution Wf.

Accordingly, the emitted radiation 130 contains radiation having both the first spectral distribution Wi and the second spectral distribution Wf.

The spectral shift between the spectral distribution Wib of the illumination beam 120 and the second spectral distribution Wf is caused by the fluorescent properties of the labeling agents. The spectral shift is also referred to as the Stokes shift.

The labeling agents are characterized by a wavelength interval in which the labeling agents are most efficiently excited so that they will respond with a fluorescent emission. Accordingly, the labeling agents are most efficiently excited when the spectral distribution Wib of the illumination beam 120 corresponds to the wavelength interval in which the labeling agents are most efficiently excited. The fluorescent emission generates the scattered radiation having the second spectral distribution Wf.

The labeling agents may for instance be excitable in a wavelength interval including a wavelength of 400 nm. If the labeling agent has a spectral shift of for example 200 nm, the labeling agent will respond with a fluorescent emission having a second spectral distribution located in the vicinity of 600 nm when the labeling agent is illuminated with radiation having a spectral distribution with a center wavelength of approximately 400 nm.

The center wavelength of the spectral distribution may for instance be understood as the wavelength where the radiation of the spectral distribution has the largest intensity.

Different labeling agents can be used for labeling molecules of samples 110 of biological material. For instance quantum dots, fluorophores, chromophores, dyes, luminescent nanoparticles, nanorods, beads and gold particles can be used as labeling agents.

Quantum dots can be either metal of semiconductor nanoparticles, where the particle diameter is so small that the effect of quantum confinement gives rise to unique optical and electronics properties that are not available and electronic properties that are not available in either discrete atoms or in bulk solids. Quantum dots have the advantage of a broadband absorption spectrum, in contrast to e.g. fluorophores. The absorption of a photon with energy above the bandgap energy results in the creation of an electron-hole pair (or exciton). The absorption has an increased probability at higher energy (i.e., shorter wavelengths) and therefore results in a broad-band absorption spectrum. The radiative recombination of an exciton leads to the emission of a photon in a narrow symmetric energy band. The long life time of the exciton (usually larger than 10 ns) and the narrow emission spectrum of quantum dots are advantageous over e.g. fluorophores.

There exists a large number of types of quantum dots; for instance InP quantum dots that are tuneable to emit wavelengths anywhere below 915 nm, silicon quantum dots, quantum dots synthesized from semiconductor materials such as CdS, CdSe, and CdTe (II-VI materials); InP and InAs (III-V materials); PbSe (IV-IV materials).

The types of labeling agents are not limited to those types mentioned above and, therefore, other types of luminescent agents may equally be used for labeling samples 110. Similarly, the list of quantum dots are not limited to those mentioned above, since quantum dots synthesized from other materials may equally be used.

The labeling agent should not necessarily be understood as only comprising luminescent or fluorescent agents, such as quantum dots. That is, in order for the labeling agent to conjugate, or bind, to molecules of the sample 110, the luminescent agents of the labeling agent may be interfaced with tags that are capable of binding to molecules of the sample 110. Such tags comprise recognition moieties, ligands, and charged adapter molecules that interface with the luminescent or fluorescent agents via electrostatic interactions. Other conjugation method comprise covalent attachment and thiol-exchange reaction. An example of how to conjugate biomolecules to quantum dots comprises a 50 µl quantum dot solution (2 µM), 30 µl EDC (100 mM), 30 µl sNHS (100 mM) and 90 µl protein (15 µM), followed by incubation for 2 hours and subsequent purification with a spinfilter. Details of how labeling agents binds to molecules, targets or probes, can be found, for instance, in the reference: Nanotechnologies for the life sciences, Volume 1: "Biofunctionalization of Nanomaterials", Edited by Challa Kumar, Wiley-VCH, 2005.

Figure 2:
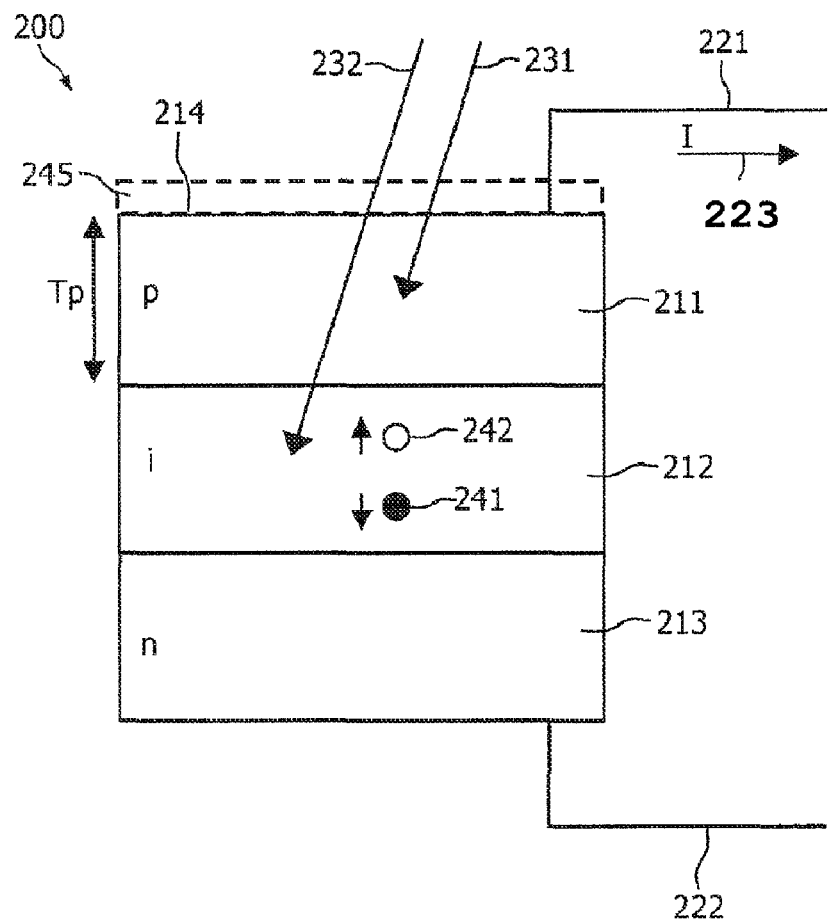
FIG. 2 is an illustration of a PIN photodiode according to the present invention.

FIG. 2 is an illustration of a PIN photodiode 200 comprising a first semiconductor layer 211 doped with a first type of impurities, an intrinsic (un-doped) semiconductor layer 212 and a second semiconductor layer 213 doped with a second type of impurities.

When the first semiconductor layer 211 is doped with an acceptor impurity having less electrons than are needed to bond it to the semiconductor material, the first semiconductor layer 211 is referred to as a p doped layer, because the acceptor impurity can accept one or more electrons from the valence band. Thus, the acceptor impurity becomes a negative ion, and a free hole is generated in the valence band.

When the second semiconductor layer 213 is doped with a donor impurity having more valence electrons than are needed to bond it to the semiconductor material, the second semiconductor layer 213 is referred to as an n doped layer. The donor impurity becomes a positive ion and a free electron is generated in the conduction band.

The intrinsic layer 212 contains no net acceptor or donor impurities, and therefore has no free holes in the valence band or free electrons in the conduction band. This makes it electrically a highly resistive material.

The top of the valence band and the bottom of the conduction band are separated in energy by the so-called bandgap, Eg. In crystalline semiconductors this is a region of energies which are forbidden, that is to say that electrons may not have energies which reside within this the band gap. In amorphous semiconductors there is a continuous density of states in the band gap but the density of states is very small, typically five or six orders of magnitude less than at the band edges. When a photon is incident on a semiconductor it will be absorbed if the photons energy can promote an electron from the valence band to an allowed energy state. In crystalline semiconductors there are effectively no allowed states in the bandgap and in amorphous semiconductors the density of states in the bandgap is so low that an allowed transition within the bandgap is very unlikely. This means that for both crystalline and amorphous semiconductors strong optical absorption will only happen if the photon energy is large enough to excite an electron from the valence band directly to above the conduction band edge. This excitation moves that electron into the conduction band, where it becomes a free electron, and leaves behind a free hole in the valence band. This is known as electron-hole pair generation.

It should be understood that a photon or radiation may be absorbed in any of the first semiconductor layer 211, the intrinsic layer 212 or the second semiconductor layer 213.

If the electron-hole pair is formed in a region with no or little electric field then the electron and hole will tend to remain in close spatial proximity and recombine, giving no useful signal to a sensor. If they are generated in a region with strong electrical field then they will have a good chance of separating before they can recombine and being extracted at the electrodes to contribute to the detector signal. The electric field can be applied externally or be the result of band bending in the intrinsic layer 212 due to electrical contact between the doped regions and the intrinsic silicon. Electron-hole pairs generated in the heavily doped regions, such as the n and p regions of the device do not produce appreciable current. In the case of n regions, this is because the conduction band already contains a high density of electrons donated by the impurity ions, and one of these recombines with the hole very rapidly, thus canceling out the pair generation. Additionally, the field in the n region is very low, because it is highly conducting, and so the force acting to move the hole toward the wire before it recombines is very small. Likewise, in the p region a high density of holes produces rapid recombination of the electron generated by the photon. However, in the intrinsic region there are no free carriers to recombine the electron-hole pair, and carrier separation is swift because the material is less conducting than the doped regions and therefore has a higher field gradient. Therefore, in the intrinsic layer 212 the free electron 241 is able to migrate to the n doped layer and the free hole 242 is able to migrate to the p doped layer where they are collected and then pass out through the wires 221 and 222 as a current I, which direction is indicated by the arrow 223.

In FIG. 2 the photodiode is arranged so that the incident radiation 231 and 232 being emitted from the sample 110 of biological material is impinging the top face 214 of the p doped layer 211. Accordingly, the top face 214 may be adapted to receive incident radiation.

An antireflection coating 245 may also be applied on the top face 214 of the p layer. The antireflection coating 245 is capable of increasing the amount of incident radiation that is transmitted into the p doped layer. The antireflection coating is optional and need not be provided on the top face 214 of the p layer.

In FIG. 2 the incident radiation 231 illustrates incident radiation having the first spectral distribution Wi and the incident radiation 232 illustrates radiation having the second spectral distribution Wf. Due to the difference in wavelengths of the first and second spectral distributions, and due to a wavelength dependency of the absorption properties of the p, n and intrinsic layers of the photodiode, different wavelengths will be transmitted to different layers and different depths within the layers of the photodiode. As illustrated in FIG. 2, the incident radiation 231 having the first spectral distribution Wi (for instance towards the blue end of the spectrum) will be fully absorbed, or at least substantial fully absorbed, in the p layer 211. The incident radiation 232 having the second spectral distribution Wf (for instance towards the red end of the spectrum) will be transmitted through the p layer and into the intrinsic layer. Thus, the incident radiation 232 will be partly absorbed in the p layer, while the remaining radiation 232 will be transmitted into the intrinsic layer 212 where it will be absorbed.

The percentage of absorption in the p layer of incident radiations 231 and 232 having first and second spectral distributions, depends on the thickness Tp of the p layer and the wavelengths of the first and second spectral distributions, Wi and Wf.

The semiconductor layers 211-213 of the photodiode 200 can be manufactured for instance by depositing amorphous silicon by Plasma Enhanced Chemical Vapour Deposition (PECVD). The deposition rate for producing amorphous silicon layers 211-213 of the photodiode 200 can for instance vary between 10 nm/min and 100 nm/min.

The electrical contact between the wires 221-222 and the first and second semiconductor layers 211 and 213 may be provided with a metallic ring contract having a center aperture or by depositing a transparent conducting material on the faces, e.g. the top face 214. For instance the transparent conducting material may be Indium Tin Oxide.

Details of the physics of photodiodes can be found, for instance, in the reference: Semiconductor Devices, Physics and Technology, 2nd edition, S. M. Sze. Particular in-depth consideration of hydrogenated amorphous silicon photodiodes can be found, for instance, in the reference: Hydrogenated amorphous silicon, R. A. Street.

Figure 3:
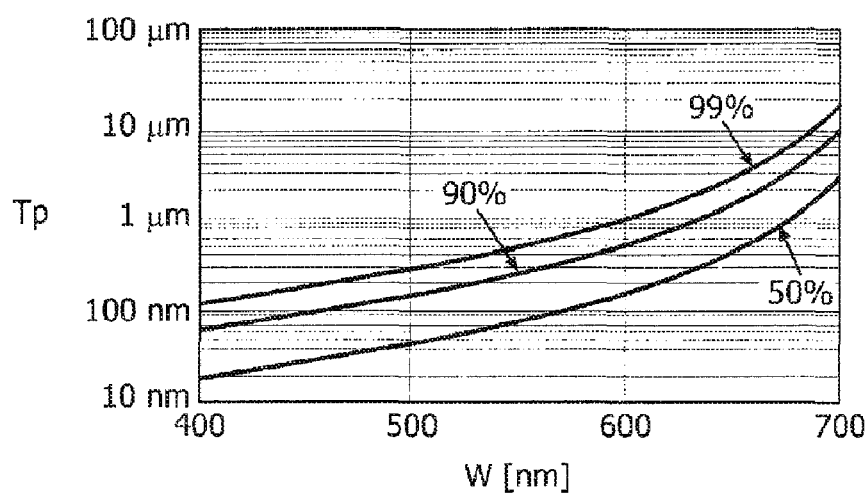
FIG. 3 shows graphs showing the relation between the p layer semiconductor thickness and the wavelength of the incident radiation according to the present invention.

FIG. 3 shows graphs showing the relation between the thickness Tp of the p layer 211 and the wavelength W of the incident radiation for different percentages of absorbed radiation in the p layer. The graphs in FIG. 3 are representative for p layers made of p-doped amorphous silicon, a-Si. The abscissa shows the wavelength W of the incident light and the ordinate shows the thickness of the p layer. The three curves labeled with percentages 50%, 90% and 99%, show the thicknesses Tp, where 50%, 90% and 99% of the incident radiation has been absorbed, as a function of wavelength W. As outlined in relation to FIG. 2, absorption in the p layer does not contribute significantly to the photocurrent.

From FIG. 3 it is seen that, if the incident radiation 231 having the first spectral distribution Wi close to a wavelength W of 400 nm, if the incident radiation 232 having the second spectral radiation Wf close to a wavelength W of 600 nm, and if the thickness Tp of the p layer is 100 nm, then 99% of the incident radiation having a wavelength of 400 nm will be absorbed in the p layer, whereas only 50% of the incident radiation having a wavelength of approx. 580 nm will be absorbed. In other words, 1% and 50% of the 400 nm and 580 nm radiation will be transmitted into the intrinsic layer 212.

Taking a thickness Tp of 500 nm, then substantially all incident radiation having a wavelength of 400 nm will be absorbed in the p layer 211, whereas 90% and 10% of incident radiation having a wavelength of 600 nm will be absorbed and transmitted, respectively.

It should be understood that, even though reference is made to incident radiation having for instance a wavelength of 400 nm, it should be understood that this incident radiation in practice has a spectral distribution corresponding to a wavelength of 400 nm. That is, for instance, a peak amplitude, an average spectral value or a center value of the spectral distribution may be close to, or equal to a wavelength of 400 nm.

Thus, by choosing an appropriate thickness of the p layer 211, e.g. 300 nm, then incident radiation having a particular radiation will be completely absorbed, or at least substantially absorbed within a volume of the first semiconductor layer, for instance the p layer 211.

From FIG. 3 it is possible to estimate a suitable thickness of the first semiconductor layer 211, so that the first semiconductor layer is capable of absorbing incident radiation of a particular wavelength. Thus, if the incident radiation having a first spectral distribution corresponding to a wavelength of e.g. 400 nm, then FIG. 3 shows that a thickness Tp greater than 100 nm will cause absorption of at least 99%. Similarly, a thickness greater than 200 nm will cause even greater absorption, and a thickness greater than 300 nm is likely to cause absorption greater than 99.9%. By choosing a thickness Tp of 1 µm, all, or substantially all, incident radiation with a wavelength of 400 nm or close to 400 nm, such as a wavelength of 405 nm, will be absorbed.

Thus, even if the thickness Tp of the first semiconductor layer 211 is selected in the interval from 100 nm to 1 µm, then a sufficient amount of radiation having the second spectral distribution, for instance with a wavelength of 600 nm, will be transmitted into the intrinsic layer 212 and cause a detectable photocurrent I.

In other words, the first semiconductor layer should capable of absorbing at least 80%, preferably at least 90% or more preferred at least 99% of the incident radiation having the first spectral distribution. This will ensure that radiation having the first spectral distribution, e.g. 400 nm, will be sufficiently absorbed, while radiation having the second spectral distribution will be sufficiently transmitted into the intrinsic layer 212.

For instance, the sample 110 of biological material has been labeled with a labeling agent capable of effectively absorbing radiation from the illumination beam 120 having a spectral distribution Wib corresponding to a wavelength of 405 nm. The labeling agent has a spectral shift, or Stokes shift, of approximately 200 nm so that the labeling agent emits radiation having a second spectral distribution corresponding to a wavelength of approximately 600 nm. If the first semiconductor layer has a thickness of, for instance 300 nm, then only the emitted radiation having a wavelength of 600 nm will be detected since the radiation having the wavelength of 405 nm will be absorbed in the first semiconductor layer.

Thus, even if the incident radiation having a wavelength of 405 nm has a larger intensity compared to the incident radiation having a wavelength of 600 nm, the 405 nm radiation will not disturb the detection of the 600 nm radiation. Accordingly, the incident radiation having a second spectral distribution corresponding to the 600 nm wavelength, can be detected with high resolution.

The wavelength or the center wavelength of the spectral distribution of the incident radiation of the illumination beam 120 may correspond to blue or violet-blue colors having wavelengths of 350 nm, 375 nm, 473 nm, 405 nm, 442 nm and 490 nm, which wavelengths can be generated by lasers, semiconductor lasers or light emitting diodes. Also center wavelengths of the spectral distribution of the incident radiation corresponding to ultra violet or violet colors, having wavelengths in the range from 380 nm down to 200 nm or even down to 10 nm can be used for illumination of the sample 110. Such wavelengths in the range from 380 nm down to 200 nm, for instance 262 nm, 266 nm, 349 nm, 351 nm or 355 nm, can be generated by uv lasers, uv semiconductor laser or uv light emitting diodes. Greater wavelengths in the green, red and infra-red color regions, having wavelengths from 500 nm to 830 nm and possible up to 1555 nm may also be used to excite the labeling agents.

The illumination source generating the illumination beam 120 may be a semiconductor laser, a gas laser, a discharge lamp or a light emitting diode. The list of illumination sources is not exhaustive and other illumination sources may equally be used.

Due to absorption properties of the first semiconductor layer 211, the photodiode 200 is capable of detecting incident low-intensity radiation being mixed with incident high-intensity radiation, where the low-intensity radiation has a spectral distribution that is spectrally shifted from the spectral distribution of the high-intensity radiation. Thus, the photodiode has spectral filtering capabilities so that the photodiode is capable of filtering out radiation having a particular spectral distribution.

Even without using expensive optical filters, for instance color filters, dichroic filters or Fabry-Perot etalons, the photodiode 200 is capable of performing optical filtering corresponding to such optical filters. At the same time a simple and cheap photo detector is achieved, because no additional optical filters are required and no mounting of such optical filters is required. Thus, a simple, compact photo and cheap photo detector has been achieved by utilizing the absorbing capabilities of the first semiconductor layer 211.

The first semiconductor layer 211, the intrinsic layer 212 and the second semiconductor layer 213 can be made of different semiconductor materials; for instance amorphous silicon (a-Si), amorphous silicon carbide (a-SiC), microcrystalline Si, materials used in the plastic/polymeric electronic technology, and crystalline silicon known from traditional crystalline technology used in production of integrated circuits. Also, low temperature polySi produced by, for instance, laser annealing of amorphous silicon may be used for the semiconductor layers. The choices of semiconductor materials is not limited to the above-mentioned materials, for instance other amorphous silicon alloys could be used. Also, for instance the first semiconductor layer 211 can be made of material that is different from the material used for the second semiconductor layer 213.

The materials used for doping the first semiconductor layer 211 and the second semiconductor layer 213 can be acceptor and donor impurities respectively, from groups 3 and 5 of the periodic table, again respectively. The most often used acceptor dopants are B, Al, Ga and In, and the most often used donor dopants are P, As and Sb. These are most readily introduced in to the amorphous silicon from the gas phase during deposition, for example by adding diborane or phosphine gas in to the PECVD reactor. Alternatively, doping is sometimes achieved by solid state diffusion, for example from an Al electrode in contact with the amorphous silicon.

The ratio of radiation powers, of incident radiation having a first spectral distribution and incident radiation having a second spectral distribution, being transmitted through the first semiconductor layer 211 can be adjusted by selection of the material used in the first semiconductor layer.

Figure 4A:
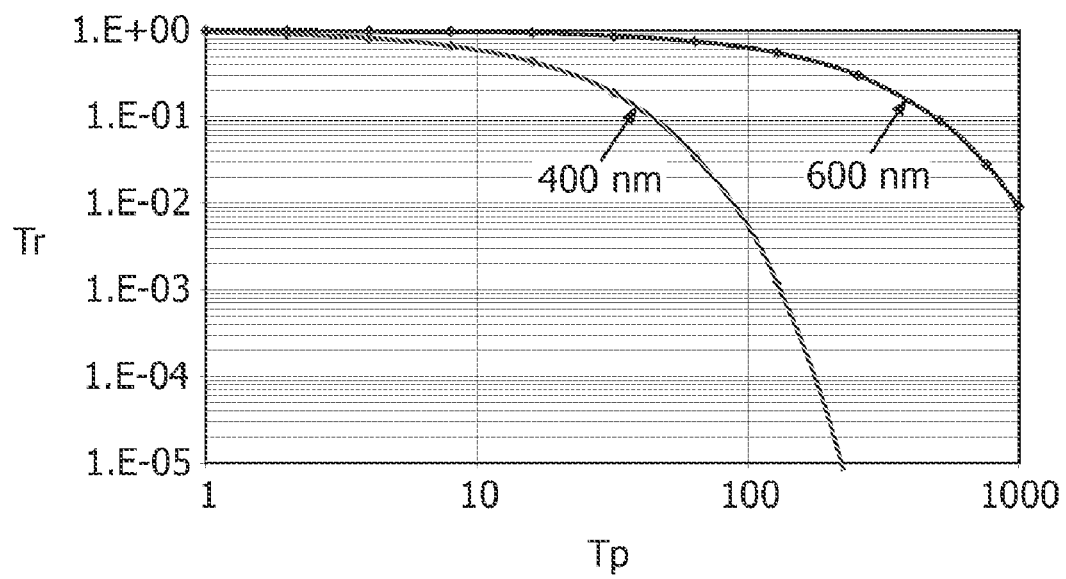
FIG. 4a shows the optical transmission of incident radiation power being transmitted through a first semiconductor layer p doped amorphous silicon according to the present invention.

FIG. 4a shows the optical transmission Tr of incident radiation power being transmitted through a first semiconductor layer 211 having a thickness Tp for 400 nm incident radiation and 600 nm incident radiation. In FIG. 4a the material of the first semiconductor layer 211 is p doped amorphous silicon (p a-Si), which typically has an optical bandgap, Eg of 1.6-1.65 eV corresponding to a radiation wavelength of approximately 775 nm.

Figure 4B:
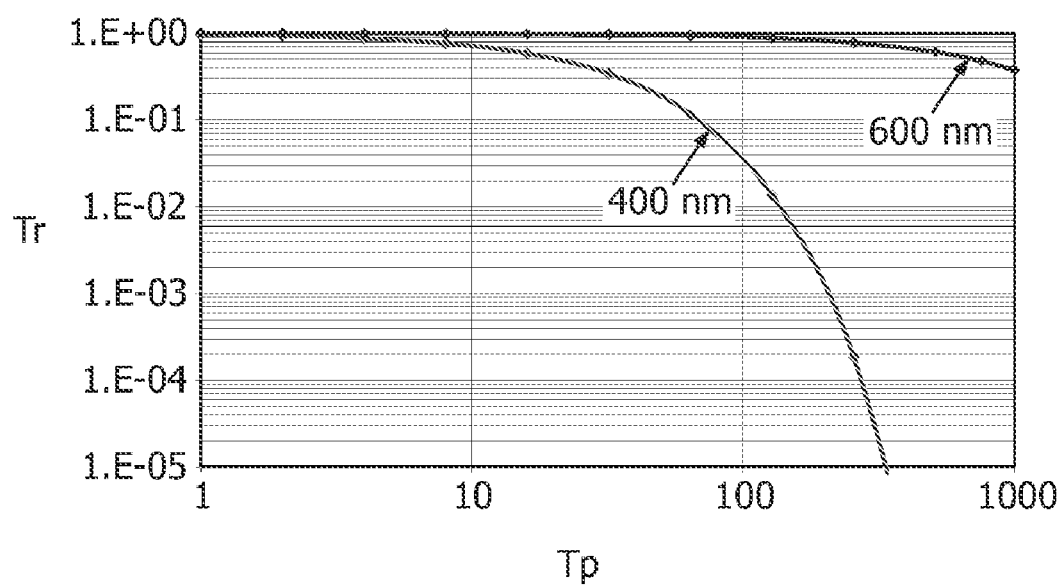
FIG. 4b shows the optical transmission of incident radiation power being transmitted through a first semiconductor layer p doped amorphous silicon carbide according to the present invention.

FIG. 4b shows similar graphs where the first semiconductor material is p doped amorphous silicon carbide (p a-SiC), which typically has an optical bandgap, Eg of 1.9 eV corresponding to a radiation wavelength of approximately 650 nm. Thus, FIG. 4b shows the optical transmission Tr of incident radiation power being transmitted through a first semiconductor layer 211 having thickness Tp, for 400 nm and 600 nm incident radiation.

Since the optical bandgap, Eg, for amorphous silicon carbide (p a-SiC) is larger than the optical bandgap for amorphous silicon (p a-Si), the optical transmissions Tr are greater in FIG. 4b than in FIG. 4a for equal thicknesses Tp. The optical transmission Tr for 600 nm radiation decreases more rapidly, as function of thicknesses Tp, in the a-Si material as compared to the a-SiC material. Therefore, the ratio of transmitted 600 nm radiation and transmitted 400 nm radiation is greater in p doped amorphous silicon carbide (p a-SiC) than p doped amorphous silicon (p a-Si).

If it is desired to increase the absorption of incident 400 nm radiation compared to transmission of 600 nm radiation, in order optimize the optical filter effect, and in order to increase the detection resolution when the incident radiation contains both 400 nm and 600 nm radiation, then p doped amorphous silicon carbide may be an preferred choice for the first semiconductor layer 211.

Figure 4C:
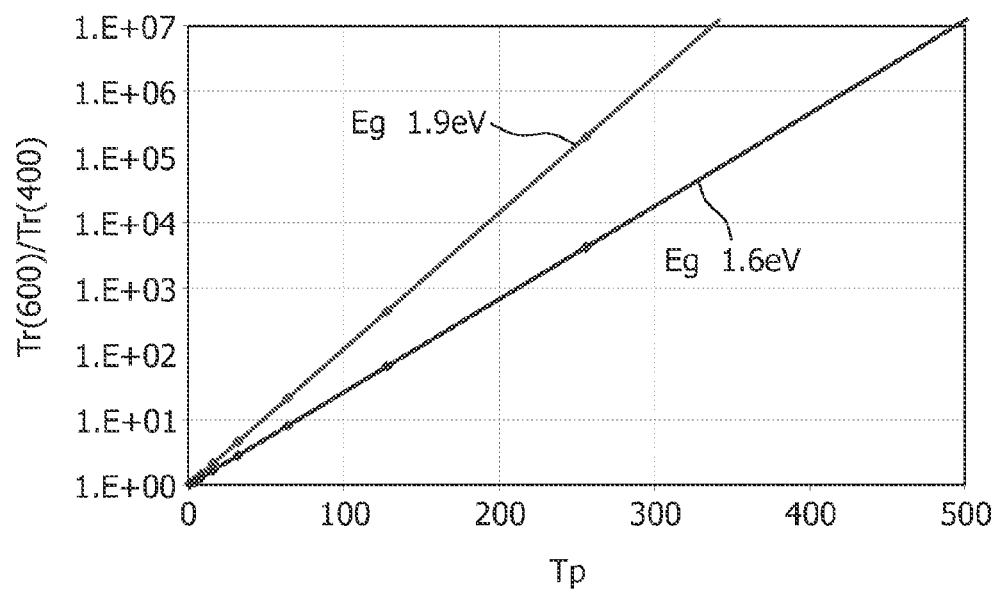
FIG. 4c shows the optical transmission ratio of radiation with wavelengths of 600 nm and 400 nm that are transmitted through semiconductor layers with different optical bandgaps according to the present invention.

FIG. 4c shows the optical transmission ratio Tr(600)/Tr(400) of radiation with wavelengths of 600 nm and 400 nm that are transmitted through semiconductor layers with optical bandgaps, Eg, of 1.6 eV and 1.9 eV as a function the layer thickness Tp. The curve labeled with Eg 1.6 eV gives the optical transmission ratio Tr(600)/Tr(400) through a layer of amorphous silicon, and the curve labeled with Eg 1.9 eV gives the optical transmission ratio Tr(600)/Tr(400) through a layer of amorphous silicon carbide. Thus, from FIG. 4c it is clear that the optical transmission ratio Tr(600)/Tr(400) increases more rapidly for a first semiconductor layer of amorphous silicon carbide than amorphous silicon.

In the example where the incident radiation having a first spectral distribution corresponding to 400 nm and the incident radiation having a second spectral distribution corresponding to 600 nm, the spectral shift or Stokes shift is approximately 200 nm. When other types of labeling agents having smaller spectral shifts are used the ratio of a transmitted radiation having second and first spectral distributions will decrease. For instance, if the wavelength of the first spectral distribution corresponds to 400 nm, and the wavelength of the second spectral distribution corresponds to 500 nm, due to a Stokes shift of 100 nm, the optical transmission ratio Tr(500)/Tr(400) will be smaller than the optical transmission ratio Tr(600)/Tr(400) for a given semiconductor material and a given thickness Tp.

Accordingly, if the spectral shift between the first spectral distribution and the second spectral distribution is at least 30 nm or 50 nm, the difference in the optical transmissions of incident radiations having the first and second spectral distributions will provide sufficient filtering effect to filter out the incident radiation having the first spectral distribution so that the incident radiation having the second spectral distribution is detectable with sufficient high resolution.

When the spectral shift between the first spectral distribution and the second spectral distribution is at least e.g. 100 nm the difference in the optical transmissions of incident radiations having the first and second spectral distributions will provide even more filtering effect so that the incident radiation having the second spectral distribution is detectable with even higher resolution.

Consequently, if the spectral shift is at least 200 nm the filtering effect will be even more pronounced so that the incident radiation having the second spectral distribution is detectable with very high resolution.

In connection with the photodiode shown in FIG. 2, the incident radiation 231 and 232 is incident on a first semiconductor layer 211 which is p-doped. Such a diode is referred to as a PIN diode. Alternatively, the first semiconductor layer 211 can be an n doped semiconductor layer and the second semiconductor layer 213 can be a p doped semiconductor layer. Even though the absorption properties of n doped semiconductor layer typically are different than a p doped semiconductor layer of the same semiconductor material, e.g. a-Si, the absorption properties of p doped semiconductor material as described in connection with FIGS. 2, 3, 4a, 4b and 4c are also applicable to n doped semiconductor material. Accordingly, the detailed description of the absorbing properties of a semiconductor layer of n-doped semiconductor material will be omitted.

Figure 5:
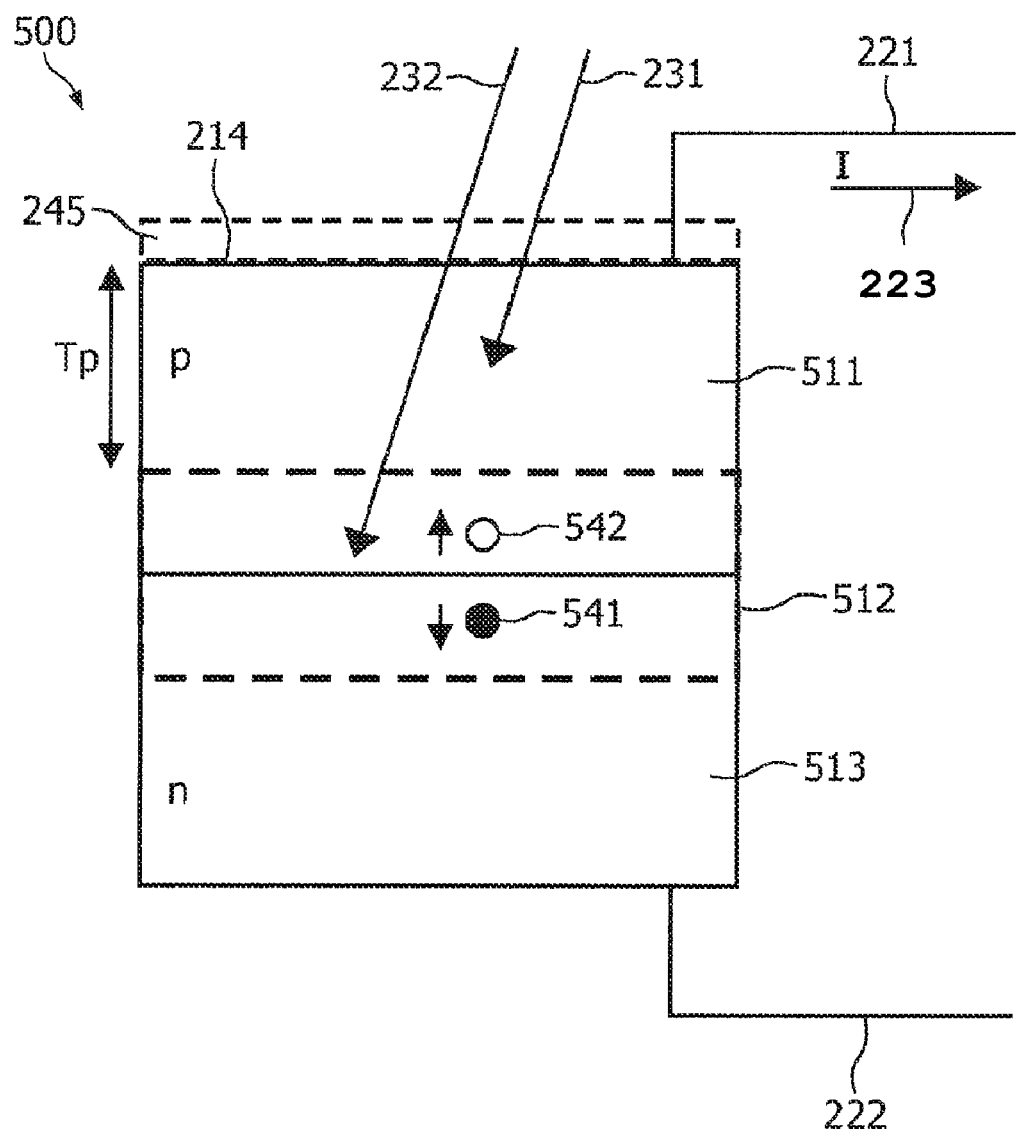
FIG. 5 is an illustration of PN type photodiode according to the present invention.

FIG. 5 is an illustration of PN type photodiode 500. The PN type photodiode 500 differs from the PIN diode illustrated in FIG. 2 mainly by having a depletion layer 512 instead of an intrinsic layer 212. Accordingly, features common for the photodiodes in FIG. 2 and FIG. 5 are assigned identical reference signs and, therefore, a detailed description of features of the PN photodiode in FIG. 5 which are identical with features of the PIN photodiode in FIG. 2 will be omitted.

The general behavior, for instance absorbing capabilities and capabilities of generating photocurrent 213, of the PN type photodiode 500 and the PIN type photodiode are equivalent, even though the PN type photodiode 500 has a depletion layer 512 and the PIN type photodiode 200 has an intrinsic layer 212. Accordingly, the depletion layer 512 and the intrinsic layer 212 can commonly be referred to as a third semiconductor region 212,512. Thus, both the PN type photodiode 500 and the PIN type photodiode 200 can be said to have a third semiconductor region 212,515 layer between the first semiconductor layer 211,511 and the second semiconductor layer 213,513.

The PN photodiode 500 comprises a first semiconductor layer 511 made of p doped semiconductor material, and a second semiconductor layer 513 made of n doped semiconductor material. The incident radiation 231 and 232 impinges directly on the top face 214 of the p doped semiconductor layer, or alternatively the incident radiation 231 and 232 may be transmitted through the antireflection coating 245 before the incident radiation impinges the top face 214.

Since the intrinsic layer 212 has been omitted in the PN photodiode, the p doped semiconductor layer 511 is brought directly into electrical contact with the n doped semiconductor layer 513.

When the p doped semiconductor layer 511 is brought directly into electrical contact with the n doped semiconductor layer 513, a third semiconductor region 512 is created which extends into both the p doped layer 511 and the n doped layer 512. The third semiconductor region 512 will be referred to as comprised by a part of the first semiconductor layer and a part of the second semiconductor layer.

The third semiconductor region 512, is referred to as the depletion layer since this layer is depleted from free electrons and holes. When a photon of the incident radiation 231 enters the third semiconductor region 512, that photon will generate a free electron 542 and a free hole 541, given that the photon has sufficient energy. The free electron 541 will travel towards and into the n doped second semiconductor layer 513, and the hole 542 will travel towards and into the p doped first semiconductor layer 511. Thus, the incident radiation 231 will generate a flow of free electrons and holes that will create a detectable current I, having the direction 213.

The p doped first semiconductor layer 511 and the n doped second semiconductor layer 513 of the PN photodiode in FIG. 5 may be reversed to form a NP photodiode where the n doped layer becomes the first semiconductor layer 511 and the p doped layer becomes the second semiconductor layer 513. Thus, in the NP photodiode, the incident radiation will impinge a top face 214 of the n doped semiconductor layer.

Figure 6:
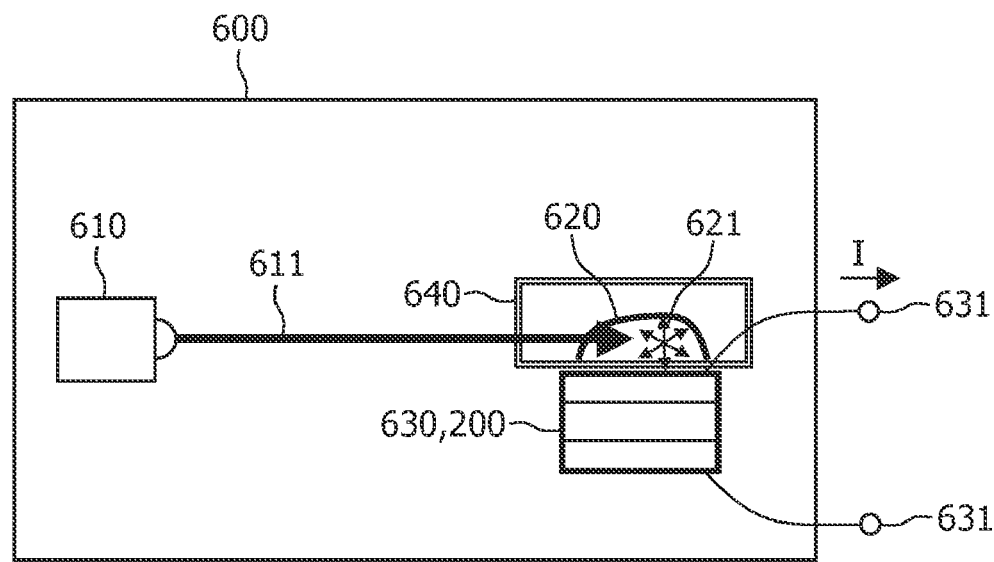
FIG. 6 is a principal sketch of a detecting apparatus capable of detecting the presence in a sample of a target molecule.

FIG. 6 is a principal sketch of a detecting apparatus 600 capable of detecting the presence in a sample 620,110 of a biological substance. The detecting apparatus 600 may also be referred to as a micro total analysis system (micro-tas), a lab-on-a-chip or a molecular diagnostic system (MDx). The detecting apparatus comprises a processing device 640. The processing device may be a transparent container that is provided with e.g. a hole for supplying the container with the labeled sample 620 comprising for instance species, molecules, antigens, antibodies, proteins, cells, tissue sections, DNA, blood and urine of the biological substance that has been labeled with labeling agents having luminescent or fluorescent properties.

The processing device 640 has been provided with probe molecules that stick to e.g. the bottom surface adjacent to the photodiode 630,200. Accordingly, the labeled target molecules of the sample 620 can react with the probe molecules that have previously been applied to the processing device. Subsequently, any non-reacted target molecules can be washed away, so the sample 620 only, or at least primarily, contains bonded target-probe pairs having labeling agents connected to them.

Any molecule of the substances comprising molecules, antigens, antibodies, proteins, cells, tissue sections, DNA, blood and urine may have the function as a target molecule. For instance, an antigen may be used as a target and an antibody may be used as a probe; or opposite an antibody may be used as a target and an antigen may be used as a probe. Accordingly, the detection apparatus may be used for instance as DNA microarrays, or immunoassays.

The detection apparatus 600 also comprises a radiation source 610, for instance a laser, a semiconductor laser, or a light emitting diode. The radiation source is capable of generating an illumination beam 611 having a spectral distribution Wib corresponding to the first spectral distribution.

The illumination beam 611 is transmitted through the transparent container 640 so that the illumination beam illuminates the sample 620. The sample 620, the processing device 640, and the labeled molecules, labeled antigens, labeled antibodies, or other labeled molecules, emits radiation 621 having the first spectral distribution and the second spectral distribution, Wi and Wf. The emission of radiation 621 may be caused by scattering, diffraction, refraction, reflection and emission of fluorescent radiation from the labeling agents.

The emitted radiation 621 is transmitted as incident radiation, comprising the first and second spectral distributions, into the photodiode 630,200 for detection of radiation having the second spectral distribution. The photodiode 630,200 generates a photocurrent I corresponding to the radiation having the second spectral distribution. The photocurrent I is provided for further analysis at the terminals 631. Alternatively, the photocurrent may be analyzed by a computer or processing unit provided in the detection apparatus 600.

Thus, by detecting and analyzing the radiation having the second spectral distribution, the presence or absence in the sample 620 of particular biological matters such as, AIDS, drugs and viruses can be determined.

The detection apparatus may also be arranged so that the processing device 640 is capable of processing the sample of a biological substance by labeling molecules of the sample 620. This can be achieved by providing the processing device with labeling agents in solid or fluid form. Accordingly, a sample 620 of the biological substance, which has not been labeled with labeling agents, can be injected into the processing device 640, so that the labeling agents that are made available by the processing device 640 will label species/molecules/antigens of the injected sample 620.

The detection apparatus 600 can be arranged for operating with labeling agents selected from the group comprising: quantum dots, fluorophores, chromophores, dyes, luminescent nano-particles, nanotubes, gold particles and beads.

The sample containing labeled or un-labeled molecules of the biological substance being supplied to the processing device 640 may be different organic materials such as cells, tissue sections, DNA, protein, blood, urine.

As is shown in FIG. 6 the direction of the illumination beam 611 is perpendicular to the normal of the surface of the first semiconductor layer 211. This is an advantage, since the illumination beam 611 will not impinge directly on the photodiode 630,200 and, therefore, the amount of radiation having the first spectral distribution, which will be incident on the photodiode 630,200, will be minimized in relation to an illumination beam 611, which is not perpendicular to the normal of the surface of the first semiconductor layer 211. However, other directions of the illumination beam 611, than the perpendicular direction, can also be used in the detection apparatus.

The detection apparatus 600 may comprise further processing devices, than the processing device 640, or alternatively other functions may be provided in the processing device 640. Thus, processing devices for amplifying a concentration of DNA by Polymerase Chain Reaction, for creating a flow of the sample 620 by use of a micro pump, separation of the sample 620 by use of electrophoresis and cell lysis for extraction of DNA may be used. Furthermore, the detection apparatus 500 may comprise microfluidic channels for processing the sample 620,110 as well as devices for washing away non-reacted target molecules.

In an application of the photodiode 200, the sample 620, 110 can be labeled with different labeling agents having different spectral shifts or Stokes shifts. For instance, labeling agents having distinct spectral shifts of 50 nm, 100 nm, 150 nm and 200 nm may be used for labeling the sample 620. For instance the labeling agents having spectral shifts of 50 nm can be connected or conjugated to a first type of molecules of the sample 110. Other labeling agents having spectral shifts of 100 nm can be connected or conjugated with a second type of molecules of the sample 620. Similarly, the other labeling agents can be conjugated with other molecules.

In order to detect the fluorescent radiation having different second spectral distributions Wif, for instance four different spectral distributions with center wavelengths of 450 nm, 500 nm, 550 nm and 600 nm, then four different photodiodes 200, each of them having particular thicknesses of their respective first semiconductor layers, can be used. For instance, a first type of photodiode 200 can have a first semiconductor layer 211 having a thickness that absorbs wavelengths up to e.g. 430 nm, so that all four spectral distributions are detected. A second type of photodiode 200 can have a first semiconductor layer 211 having a thickness that absorbs wavelengths up to e.g. 480 nm, so that the remaining three spectral distributions (500 nm, 550 nm and 600 nm) are detected. The third type of photodiode 200 can have a first semiconductor layer 211 having a thickness that absorbs wavelengths up to e.g. 530 nm, so that the remaining two spectral distributions (550 nm and 600 nm) are detected. The fourth type of photodiode 200 can have a first semiconductor layer having a thickness so that only radiation having a spectral distribution with a center wavelength of 600 nm is detected.

Figure 7:
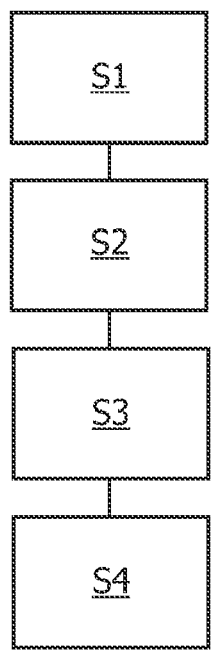
FIG. 7 is a flow-chart of a method according to the invention.

FIG. 7 is a flow chart of a method according to the invention. The method for detecting a target in a sample of a biological substance comprises the steps of:

S1: providing a detection apparatus with probe molecules for bonding with target molecules, wherein the target molecules or probe molecules are labeled with labeling agents having luminescent properties, wherein said labeling agents emits radiation having a second spectral distribution when illuminated with radiation having a spectral distribution corresponding to the first spectral distribution, S2: providing the sample containing target molecules to the detection apparatus for bonding with the probe molecules, S3: illuminating the sample with radiation having a spectral distribution corresponding to the first spectral distribution, S4: receiving emitted radiation from the sample by using a photodiode according to a first aspect of the invention, said emitted radiation comprising the first spectral distribution and the second spectral distribution.

It is to be understood that when reference is made to luminescent radiation this should be understood as including, but not limited to: fluorescence, electroluminescence, phosphorescence, reflections and diffractions. Emitted radiation should be understood as including, but not limited to scattered, reflected, diffracted, luminescent and/or fluorescent radiation. Also, a reference to a molecule should equally be understood as a macro-molecule, a group of connected molecules, and fractions of molecules.

Although the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The invention claimed is:

1. A photodiode for receiving incident radiation emitted from a target molecule of a sample of a biological substance, the photodiode comprising:
   a first semiconductor layer doped with a first impurity for receiving said incident radiation of visible light having a center wavelength of at least 350 nm and first and second spectral distribution, the first spectral distribution is spectrally shifted from the second spectral distribution,
      transmitting the incident radiation having the second spectral distribution, and
      absorbing the incident radiation having the first spectral distribution;
   a second semiconductor layer doped with a second impurity; and
   a semiconductor region for generating free electrons and free holes when excited with at least part of the incident radiation having the second spectral distribution thereby generating a photocurrent.

2. The photodiode according to claim 1, wherein the first semiconductor layer has a thickness to absorb the radiation having the first spectral distribution within a volume of the first semiconductor layer.

3. The photodiode according to claim 2, wherein the thickness of the first semiconductor layer is greater than one of 100 nm, 200 nm, and 300 nm.

4. The photodiode according to claim 1, the first semiconductor layer absorbing an amount selected from at least 80%, at least 90%, or at least 99% of the incident radiation haying the first spectral distribution.

5. The photodiode according to claim 1, wherein the semiconductor region is a layer of intrinsic semiconductor material positioned between the first semiconductor layer and the second semiconductor layer.

6. The photodiode according to claim 1, wherein the first impurity is a p type acceptor impurity and the second impurity is an n type donor impurity.

7. The photodiode according to claim 1, wherein the target molecule is labeled with labeling agents having luminescent properties.

8. The photodiode according to claim 7, wherein the labeling agents causing the spectral shift between the first spectral distribution and the second spectral distribution.

9. The photodiode according to claim 1, wherein the spectral shift between the first spectral distribution and the second spectral distribution is one of at least 50 nm, at least 100 nm, and at least 200 nm.

10. The photodiode according to claim 1, wherein at least one of the first semiconductor layer and the second semiconductor layer is made of a material selected from the group comprising: a-Si, a-SiC, microcrystalline Si and low temperature polySi.

11. The photodiode according to claim 1, wherein an anti-reflection coating is applied on a top face of the first semiconductor layer.

12. A detecting apparatus for detecting at least one of presence, absence, and quantity of a target molecule of a sample of a biological substance, said detecting apparatus comprising:
   a processing device provided with the sample having target molecule and probe molecules for bonding with the target molecules in the sample;
   labeling agents having luminescent properties for labeling the target and probe molecules in the sample;
   an illuminator for illuminating the sample with radiation of visible light having a first spectral distribution, said labeling agents emitting radiation having a second spectral distribution when illuminated with the radiation; and
   a photodiode for receiving incident radiation emitted from a target molecule of the sample when the sample having target molecules is illuminated by the illuminator, the photodiode having
   a semiconductor region to generate free electrons and free holes when excited with at least part of the incident radiation having the second spectral distribution thereby generating a photocurrent,
   a second semiconductor layer doped with a second impurity having more valence electrons than are needed for bonding to semiconductor material, and
   a first semiconductor layer doped with a first impurity
      to receive the incident radiation of visible light comprising the first spectral distribution and the second spectral distribution, the first spectral distribution spectrally shifted from the second spectral distribution, to absorb at least 80% of the incident radiation having the first spectral distribution without significantly contributing with a photocurrent, and to transmit the incident radiation having the second spectral distribution that excites free electrons and free holes in the semiconductor region to generate a detectable photocurrent.

13. The detection apparatus according to claim 12, wherein the direction of the radiation from the illuminator is perpendicular to the normal of the surface of the first semiconductor layer.

14. The detection apparatus according to claim 12, wherein said labeling agents comprise a quantum dot.

15. The detection apparatus according to claim 12, wherein the sample of the biological substance comprises substances selected from the group comprising: cells, tissue sections, DNA, blood, urine.

16. The detection apparatus according to claim 12, further comprising a second processing device for amplifying a concentration of DNA by Polymerase Chain Reaction.

17. A method for detecting a target in a sample of a biological substance, said method comprising acts of:

bonding probe molecules with target molecules in the sample;

labeling the target molecules and/or probe molecules in the sample with labeling agents having luminescent properties;

illuminating the sample with the radiation of visible light having a spectral distribution corresponding to the first spectral distribution, said labeling agents emitting radiation having a second spectral distribution when illuminated with the radiation; and receiving incident radiation of visible light emitted from a target molecule of the sample when the sample having target molecules is illuminated on a photodiode having a semiconductor region to generate free electrons and free holes when exited with at least part of the incident radiation having the second spectral distribution thereby generating a photocurrent, a second semiconductor layer doped with a second impurity having more valence electrons than are needed for bonding to semiconductor material, and a first semiconductor layer doped with a first impurity to receive the incident radiation comprising the first spectral distribution and the second spectral distribution, the first spectral distribution spectrally shifted from the second spectral distribution, to absorb at least 80% of the incident radiation having a first spectral distribution without significantly contributing with a photocurrent, and to transmit the incident radiation having a second spectral distribution that excites free electrons and free holes in the semiconductor region to generate a detectable photocurrent.

* * * * *